United States Patent [19]

Zeldis et al.

[11] Patent Number: 5,073,481
[45] Date of Patent: Dec. 17, 1991

[54] ASSAY TO DETECT THE PRESENCE OF LIVE VIRUS IN VITRO

[75] Inventors: Jerome B. Zeldis, Newton Highlands, Mass.; Robert P. Gale, Bel Air, Calif.; Howard N. Steinberg, Brookline, Mass.

[73] Assignee: Beth Israel Hospital Association, Boston, Mass.

[21] Appl. No.: 443,823

[22] Filed: Nov. 30, 1989

Related U.S. Application Data

[63] Continuation of Ser. No. 175,682, Mar. 21, 1988, abandoned, which is a continuation of Ser. No. 893,678, Aug. 6, 1986, abandoned.

[51] Int. Cl.$^5$ .......................... C12Q 1/70; C12Q 1/02; C12N 7/04; A61K 39/12
[52] U.S. Cl. .......................... 435/5; 435/29; 435/236; 436/820; 424/89
[58] Field of Search ................... 435/5, 29, 235, 236, 435/235.1; 436/820; 424/89, 101

[56] References Cited

U.S. PATENT DOCUMENTS

| | | | |
|---|---|---|---|
| 4,230,697 | 10/1980 | Nishida et al. | 514/8 |
| 4,783,407 | 11/1988 | Provost et al. | 435/35 |
| 4,952,494 | 8/1990 | Zeldis et al. | 435/5 |

OTHER PUBLICATIONS

Zeldis et al., J. Clin. Invest., vol. 78, 1986, pp. 411–417.
Young et al., The J. Clin. Invest., vol. 73, 1984, pp. 224–230.
Yoffe et al., J. Infect. Dis., 153(3), 471–477 (1986).
Pontisso et al., Br. Med. J., 288: 1563–1566 (1984).
Elfassi et al., Proc. Nat'l Acad. Sci. USA, vol. 81, pp. 3526–3528 (1984).
Lie-Injo et al., DNA, 2(4), 301–307 (1983).
Laine et al., Science (USA), 229: 561–563 (1985).
Romet-Lemonne et al., Science, vol. 221, pp. 667–669, Aug. 1983.
Young et al., The Journal of Clinical Investigation, Inc., vol. 73, pp. 224–230, Jan. 1984.
Tabor et al., J. Med. Virol., 11(1), 1983, pp. 1–10.
Alberts et al., Molecular Biology of the Cell, 1983, Garland Publishing, Inc., pp. 921–924.
Romet-Lemonne et al., "Hepatitis B Virus Infection in Cultured Human Lymphoblastoid Cells", Science, vol. 221 (Aug. 1983).
Young et al., "Characterization of a Virus that Causes Transient Aplastic Crisis", The Journal of Clinical Investigation, Inc., vol. 73 (Jan. 1984).
J. B. Zeldis, H. Mugishima, R. P. Gale, H. Steinberg, "Hepatitis B Virus Inhibition of Bone Marrow Stem Cells", Gastroenterology, vol. 90, May 1986, p. 1783.

Primary Examiner—Esther L. Keeplinger
Assistant Examiner—Jacintha M. Stall
Attorney, Agent, or Firm—Lorusso & Loud

[57] ABSTRACT

An assay to detect the presence of live hepatitis viruses in vitro. Bone marrow cells of leukemic cell line cells are exposed to a body fluid or biological preparation to be tested and the cells are placed in suspension. When using bone marrow cells, growth factors to the bone marrow stem cells are added. It has been determined that presence of a live hepatitis virus suppresses the growth of colonies of the stem cells. Therefore, if the number of colonies growing in the mixture are less than that number present in a culture of cells exposed to a sample that has been determined to contain no live virus, live hepatitis virus is present in the sample tested. The assay is particularly useful to determine the presence of live hepatitis B virus in a vaccine.

24 Claims, 3 Drawing Sheets

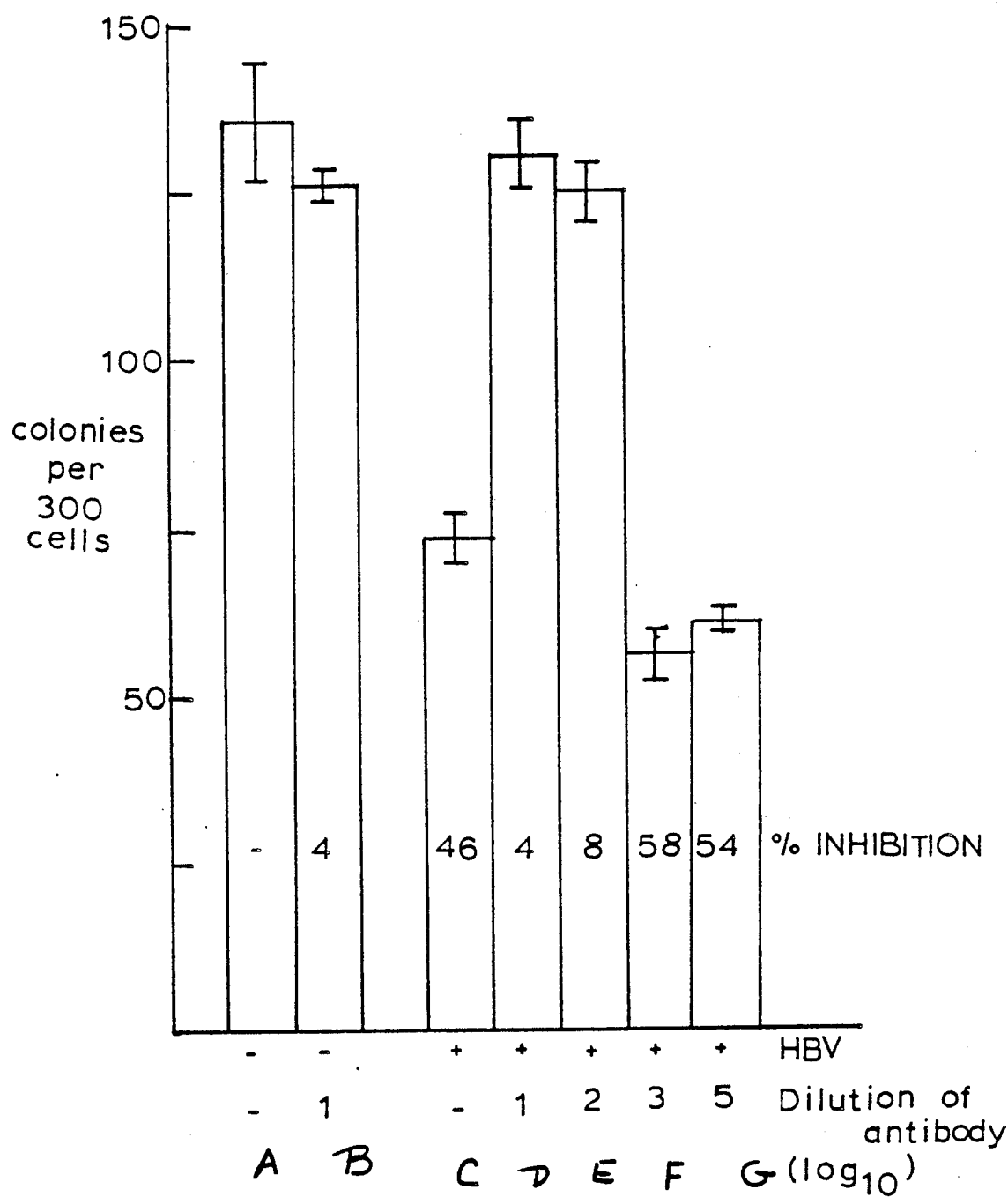

ASSAY TO DETECT THE PRESENCE OF LIVE VIRUS IN VITRO

This is a continuation of copending application Ser. No. 07/175,682 filed on Mar. 21, 1988, now abandoned which is a continuation of copending application Ser. No. 893,678 filed on Aug. 6, 1986, now abandoned.

BACKGROUND OF THE INVENTION

The present invention is a method to detect the presence of a live virus in a sample, and more particularly, a method to detect the presence of live hepatitis viruses, especially hepatitis B virus, in a body fluid, such as serum, or in a biological preparation, such as a vaccine.

In simplest terms, a vaccine for injection into a mammal for immunization from a disease contains weakened or dead viruses. The injection of the weakened or dead virus into the mammal causes natural antibodies to develop within the mammal and ultimately results in an immunization by that mammal toward the live virus.

It is essential to the proper use of any vaccine that it does not contain any live virus that could cause disease. Of course, since the vaccine is actually made from a live virus which is either weakened or killed, there is a possibility that the vaccine might contain an infectious virus. Injecting an infectious virus into a primate would contribute toward the primate's contracting the particular disease and therefore would not accomplish the objective disease.

Accordingly, a vaccine must be tested to determine whether or not any infectious virus is present. At this time, there is no known way to detect the presence of many infectious viruses, including hepatitis viruses, in a sample except for a very costly and time consuming use of primates. Essentially, the vaccine is injected into a chimpanzee and after waiting a period of time of approximately one year, if the chimpanzee does not develop the disease, the vaccine is considered safe. This process is time consuming, as a sufficient period of time must go by to ensure that the disease does not surface in the animal. The method is expensive as each animal used is expensive and cannot be used more than once.

Besides vaccines, humans receive a variety of blood products such as clotting factors that have been associated with transmitting diseases, such as viral hepatitis. A method to detect the presence of hepatitis viruses in these products would aid in ensuring the safety of these products for human use.

Viral hepatitis B is a very serious illness. A large proportion of the world's population dies from complications of this virus. The virus is transmitted perinatally, sexually, and from a variety of other sources. Because of the danger associated with the disease, there is an incentive to immunize the susceptible populations against this virus much the same way immunization against smallpox or polio has been accomplished.

At present, the chimpanzee infection model is used to detect the presence of live hepatitis B virus ("HBV") in a body fluid or biological preparation. In vitro assays are available, but they are limited to those which measure the presence of viral products, such as DNA and proteins that the virus makes. These assays do not measure the biological viability of the virus. Therefore, even when the virus is dead, these assays would still test positive for HBV because of the presence of its by-product in the sample.

Infection with hepatitis B virus can lead to chronic hepatitis, cirrhosis and primary liver carcinoma. In the past, efforts to devise an in vitro model for hepatitis B virus infection concentrated on liver cells because that is where the disease often expresses itself; the liver appears to be the major organ affected by the virus.

Recently, researchers have broadened their search and HBV DNA has been detected in the kidney, pancreas, spleen, vascular endothelium, skin and semen of infected patients. It has also been shown that circulating mononuclear cells of chronically infected patients contain HBV DNA. Romet-Lemonne et al have found that a small percentage of bone marrow cells from infected patients contained hepatitis B virus surface antigen (HBsAg) and hepatitis B core antigen (HBcAg). See, Romet-Lemonne et al, "hepatitis B virus infection in cultured human lymphoblastoid cells", *Science* 221: 667–669 (1983). Yet, to this date a reliable in vitro model to determine the presence of live hepatitis B virus has not been developed.

Recently, Young et al demonstrated that in blood of people who are diagnosed as having severe anemia (a disease which expresses itself by noticeable suppression of the growth and differentiation of bone marrow cells), a virus was present which inhibited the growth and differentiation of certain bone marrow stem cells (CFU-E). Young et al developed an in vitro assay that detects the inhibition of growth of the stem cell when exposed to a sample containing the virus to indicate the presence of the virus. See, N. S. Young et al, "Characterization of a Virus that Causes Transient Aplastic Crisis", *Journal of Clinical Investigation*, 73:224–230, 1984. This assay was not successful, however, to detect the presence of hepatitis B virus in vitro; sera from patients with HBV-associated hepatitis failed to inhibit the growth and differentiation of bone marrow stem cells.

Accordingly, it is an object of the present invention to provide an assay to detect the presence of live virus in vitro.

It is another object of the present invention to provide an economic and accurate assay to detect the presence of live hepatitis viruses in vitro.

Still another object of the present invention is to provide an assay to detect the presence of live hepatitis B virus in a vaccine.

SUMMARY OF THE INVENTION

The present invention is an effective and economic method to detect the presence of live hepatitis viruses. It is especially good for the detection of live hepatitis B virus. The method comprises exposing mononuclear cells derived from bone marrow or blood in vitro to a sample to be tested for live virus. The cells are then suspended in semi-solid media in the presence of growth factors that promote the proliferation and differentiation of hematopoietic stem cells. After a period of time, the stem cells will form a clump of cells called a colony. Depending on the type of growth factors added to the cells, different types of bone marrow stem cell colonies can be detected. The number of colonies detected after exposure to hepatitis viruses is less than those present in cultures of bone marrow cells exposed to a sample that lacks the virus. Similar assays can be performed using leukemic cell line cells rather than the mononuclear cells.

These and other objects of the invention will be shown from the following detailed description of the invention, together with the drawing.

BRIEF DESCRIPTION OF THE DRAWINGS

FIG. 4 illustrates the inhibitory effect of hepatitis B virus on leukemic cell lines as noted in the assay of the present invention, and the reversal of that effect when antibodies to the hepatitis B virus are introduced.

DETAILED DESCRIPTION OF THE INVENTION

Figure 1:
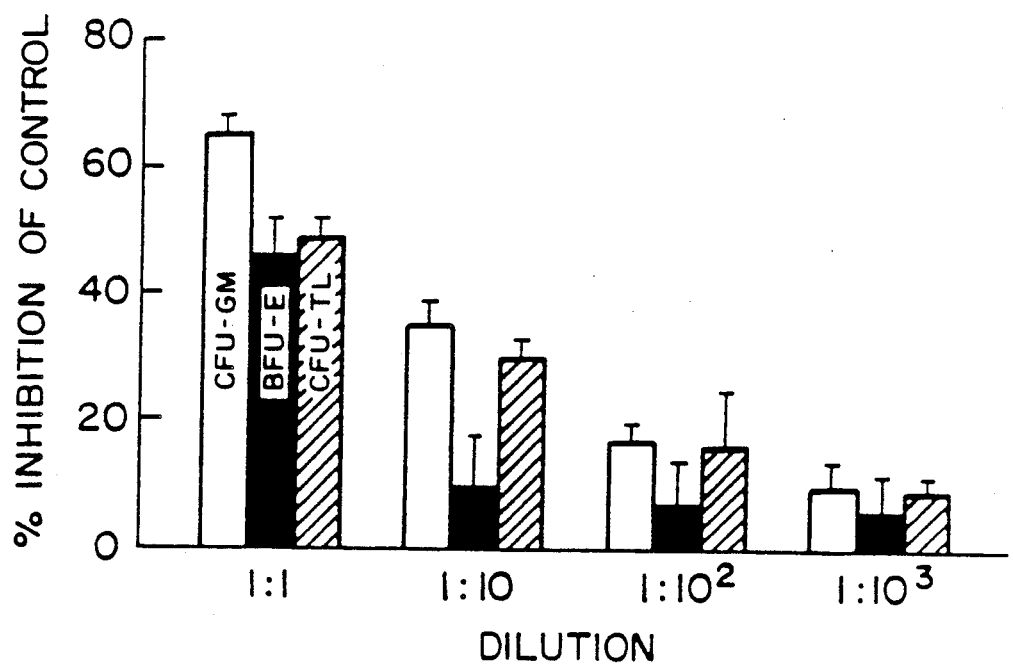
FIG. 1 illustrates the inhibitory effect of hepatitis B virus on the growth of certain bone marrow stem cells as noted in the assay of the present invention.

It has been determined that in vitro exposure of human bone marrow to hepatitis viruses results in a dose-dependent inhibition of the bone marrow stem cells that will ultimately differentiate into red blood cells (CFU-GEMM), BFU-E, CFU-E), granulocytes (CFU-GEMM, CFU-GM), monocytes (CFU-GEMM, CFU-GM), platelets (CFU-GEMM), lymphocytes (CFU-$T_L$) and bone marrow fibroblasts (CFU-$F_N$). Furthermore, hepatitis viruses inhibit in vitro colony formation of leukemic cell lines. With those findings in mind, methods have been devised to determine the presence of live hepatitis viruses in vitro. One method using mononuclear cells comprises (1) exposing the mononuclear cells from bone marrow or blood in vitro to a sample that potentially contains the virus, (2) placing the mixture in suspension culture, (3) inducing the cells to differentiate and proliferate by adding growth factors and (4) determining the number of colonies present after an incubation period. If a live virus is present, the number of colonies is less than those found in cultures of cells exposed to no live virus.

A similar assay can be performed with leukemic cell line cells. The growth of leukemic cell line cells is not dependent on growth factors, accordingly, none are needed to stimulate the growth of the cells. Moreover, leukemic cell line cells have excellent plating or clonal efficiency. Thus, a smaller number of cells can be used in each assay to produce a sufficient number of colonies for a definitive result. The method in this instance comprises (1) exposing leukemic cell line cells to a sample that potentially contains the virus, (2) placing the mixture in suspension culture and (3) determining the number of colonies present after an incubation period. Again, if a live virus is present, the number of colonies is less than those found in cultures of cells exposed to no virus.

First, leukemic cell line cells or mononuclear cells are preincubated to or coincubated to a sample that potentially contains live hepatitis viruses. Leukemic cell line cells can be obtained from the American Type Culture Collection in Rockville, Md. Any leukemic cell line may be used; the K562 cell line is preferred. Mononuclear cells are obtained from bone marrow donors who have no serologic evidence of previous or present hepatitis virus infections. The mononuclear fraction of the human bone marrow cells is isolated by conventional methods, such as Ficoll-Hypaque density centrifugation and subsequently suspended in cell culture media, such as RPMI-1640, which can be obtained from Grand Island Biology Corporation, Statten Island, N.Y., ("Gibco") supplemented with fetal calf serum.

The mononuclear cells or leukemic cell line cells are then exposed to the samples to be tested for a predetermined period of time. Exposure of the cells to the sample, which potentially contains live virus, may occur in either of two ways. In one method, the cells are incubated with the sample for a period of time ranging from one hour to overnight, preferentially 16-24 hours. It is speculated that the virus is taken up by the cells. The cells are then washed free of extraneous virus. The cells are then suspended in semi-solid media such as plasma clot, agar, agarose or methylcellulose, using conventional techniques. See, for example, Golde D.W., *Methods in Hematology: Hematopoiesis*, New York, Edinburgh, London and Melbourne: Churchill Livingstone, pp. 1–361, 1984. Alternatively, the sample can be added to the cells directly and then placed in the suspension of semi-solid media for the conventional stem cell assays. The second method is preferred since that method involves less manipulation of the cells, and, accordingly, a reduced risk of exposure to infection for persons handling the samples.

When using mononuclear cells, growth factors specific to a particular type of stem cell are added to the suspension culture to facilitate the differentiation and proliferation of the hematopoietic stem cells so that only that type of stem cell can form a colony. The growth factors, culture conditions and guidelines for what constitutes a colony are well established hematological teaching. See, the Golde reference, discussed above. Leukemic cell line cells do not require the use of growth factors but will proliferate in culture without them. Since progenitor cells for the bone marrow cells and the leukemic cell line cells are immobilized in a semi-solid matrix, the progeny remain within a confined area. Thus, after an appropriate incubation time (7–16 days), a colony of cells will be observed. The cells are then fixed, usually with gluteraldehyde, and stained by conventional techniques such as with the Wright-Giemsan stain. The number of colonies that have grown are counted.

The number of colonies formed from cells incubated with samples that potentially contain hepatitis viruses are compared to the number of colonies formed from cells incubated with a control sample that contains no virus and the data expressed as percent inhibition. If the number of colonies formed when the sample to be tested is exposed to the cells is less than the number of colonies formed when the control sample that contains no live hepatitis viruses is mixed with the cells, it can be determined that live hepatitis virus is present in the sample. The extent of inhibition of colony formation is a function of both the multiplicity of infection (m.o.i.) (the ratio of the number of viral particles to a cell) and the time of exposure of the cells to the virus. This is true both in the case of human bone marrow stem cells and leukemic cell colony forming assays.

EXAMPLE

Bone marrow cells are obtained either from the illiac crest of normal donors or from the ribs of patients undergoing heart surgery or lung resection. Cell suspensions are prepared and are layered over Ficoll-Hypaque to separate the contaminating red blood cells and leukocytes from the desired mononuclear cells. This is effected by spinning the cells at 40 xg for 30 minutes. The enriched mononuclear cells are washed free of the Ficoll, resuspended in the plating medium RPMI-1640 supplemented with 10% heat inactivated fetal calf serum and cell numbers are adjusted to the desired concentration.

The cells are then infected with hepatitis B virus. $5 \times 10^6$ mononuclear cells in 0.1 ml suspension are incubated with 0.1 ml of sera containing $3 \times 10^7$ viral hepatitis particles for $18 \times 24$ hours at 37° C. and an atmosphere of 5% $CO_2$. Control cells are incubated with normal human serum (Type AB blood). After infection with virus, the bone marrow cells are washed free of extraneous virus by repeated centrifugation (10 minutes at 1500 RPM) the addition of fresh medium, Iscove's Modified Delbecco's Medium, which can be obtained from Gibco, ("IMDM"). Cells are finally resuspended in medium to give a concentration of $1.75$–$3.0 \times 10^6$ cells per ml. The progenitor cells are assayed as described below.

Assay for Granulocyte-Monocyte Progenitor Cells

The granulocyte-monocyte progenitor cell (CFU-GM) is a stem cell committed or programmed to undergo proliferation and differentiation giving rise to both mature granulocytes and monocytes. These CFU-GM do not give rise to any other cell type. CFU-GM are assayed as follows:

$2 \times 10^5$ mononuclear cells are plated in either alpha medium or IMDM containing 0.3% agar (Difco, Detroit, Mich.), 20% fetal calf serum and either 10% Giant Cell phytohemagglutinin-stimulated leukocyte conditioned medium (PHA-LCM). Both GCT and PHA-LCM are a source of colony stimulating activity allowing the progenitor cells to undergo proliferation and differentiation so at the end of 10 days of culture at 37° C. in a 5% $CO_2$ atmosphere, discrete colonies of 40 cells or greater can be scored. PHA-LCM is prepared by the addition of 1% phytohemagglutinin (Wellcombe Company, Triangle Park, N.C.) to Ficoll-Hypaque separated peripheral blood mononuclear cells. The conditioned medium is harvested after seven days of culture at 37° C. and 5% $CO_2$, sterile filtered and stored at $-20°$ C.

Assay for Mature (CFU-E) and Primitive (BFU-E) Erythroid Progenitor Cells

Both CFU-E and BFU-E are progenitor cells that are committed to differentiating into mature red blood cells. The two stem cells are distinguised by physical characteristics, their response to erythropoietin, a growth factor, and the time of their appearance in culture. Both erythroid progenitor cells may be assayed either in a methylcellulose or a plasma clot type matrix.

For methycellulose assays, $2 \times 10^5$ mononuclear cells are cultured in IMDM in 0.8% methycellulose, 30% fetal calf or human type AB serum, 10% PHA-LCM, $5 \times 10^{-5}$ mercaptoethanol, 1% deionized Bovine serum (Sigma, St. Louis, Mo.) and erythropoietin. Erythroportin (EPO) is the hormone that allows both CFU-E and BFU-E to give rise to colonies of red blood cells in this culture. As CFU-E are more sensitive to the effect of EPO, only 0.3 u/ml are required to assay for CFU-E. 2 u/ml are added to cultures assaying for BFU-E. The procedure for assaying erythroid progenitor cells in plasma clot cultures is similar to the methylcellulose assay. However, bulk embryo extract and Bovine titrated plasma, which can be obtained from Gibco, are substituted for the methylcellulose. For CFU-E and BFU-E, cultures are analyzed after 7 and 14 days of culture respectively. Colonies are scored as positive for erythroid cells after staining with benzidine, a specific stain for the presence of red blood cells.

Assay for the Pluropotential Progenitor Cell (CFU-GEMM)

The pluropotential stem cell is a cell more primitive than the above-described progenitor cells that are already committed to a single line of blood cell development. The CFU-GEMM are not committed to a single lineage and, in cultures, can give rise to colonies consisting of mixtures of erythroid, granulocyte-monocyte and megakaryocyte cells. The technique for assay is similar to that described for erythroid cells. CFU-GEMM, however, are scored after 16 days of culture.

Assay for CFU-$T_L$

Using the methylcellulose system, the progenitor cell (CFU-$T_L$) for T-lymphocytes, which are important in immune function, can be assayed. CFU-$T_L$ are assayed in Alpha medium containing 20% fetal calf serum, 1% bovine serum albumin, $5 \times 10^{-5}$ M mercaptoethanol and 20% interleukin 2 (Cetus Corporation, Emeryville, Calif.). Colonies are scored after seven days.

Assay for CFU-$F_N$

This progenitor gives rise to colonies of bone marrow fibroblasts that are believed to be an important component of the bone marrow architecture and appears to play a role above. $2 \times 10^5$ bone marrow cells are plated in suspension above. $2 \times 10^5$ bone marrow cells are plated i suspension culture in IMDM with 15% fetal bovine serum. Colonies of fibroblasts adhering to the bottom of the culture dish are scored after 14 days in culture.

Assay for Leukemic Cell Line Cells

Leukemic cell lines, such as K562, HL-60 and U937 have been derived from patients with leukemia and adapted for culture so that they continue to proliferate as an immortalized cell line. As cells that are abnormal counterparts of normal blood cells, they have similarly been used as tools to study the factors regulating differentiation and the biochemical changes occuring during the differentiation process. It has been found that leukemic cell line cells are infectible with hepatitis B virus as are normal bone marrow cells. The various cell lines are readily available from a variety of laboratories such as the ATCC, and grow very well in the assays already described. Leukemic cells are harvested from stock flasks, washed twice in medium and resuspended in IMDM and 10% fetal bovine serum. Prior to culture, 30,000 leukemic cells are exposed to $3 \times 10^7$ particles of hepatitis virus contained in infected serum. The mixture is incubated overnight at 37° C. in a 5% $CO_2$ atmosphere. Control cells are exposed to normal human serum (Type AB). After culture, the cells are harvested, washed free of extraneous virus and resuspended in IMDM with 10% fetal calf serum so that the concentration of cells is approximately $3 \times 10^3$ cells/ml. The cells are then plated in plasma clot cultures so that each plasma clot culture contains 150 cells. The method for growing leukemic cell lines in plasma clot cultures has already been outlined for the growth of erythroid precursors. Colonies of leukemic cells are scored ten days after plating.

The number of colonies formed from mononuclear cells and leukemic cell line cells incubated with hepatitis B virus were compared to that incubated with the normal AB+control serum and the data expressed as percent inhibition. Each assay was run at least in triplicate and the results are reported as the mean number of colonies ± standard error of the mean and the percent inhibition of the control for each sample.

For example, FIG. 1 illustrates that exposure of bone marrow cells to an undiluted HBV DNA positive serum sample resulted in suppression of CFU-GM, BFU-E and CFU-TL colony formation by 65±3%, 46±6 and 49±3, respectively compared to the number of a negative control serum. The number of colonies for the control serum for CFU-GM was 224±41. The serial $\log_{10}$ dilutions of sera were made in RPMI-1640 media. Although the absolute number of colonies in each assay varied for different bone marrow specimens, percent inhibition was internally consistent for each experiment.

It can also be seen from FIG. 1 that incubation of bone marrow cells with serial $\log_{10}$ dilutions of HBV containing sera resulted in the gradual loss of the HBV mediated suppression. Inhibition of CFU-GM and CFU-TL was still observed using sera diluted 1:100.

Figure 2:
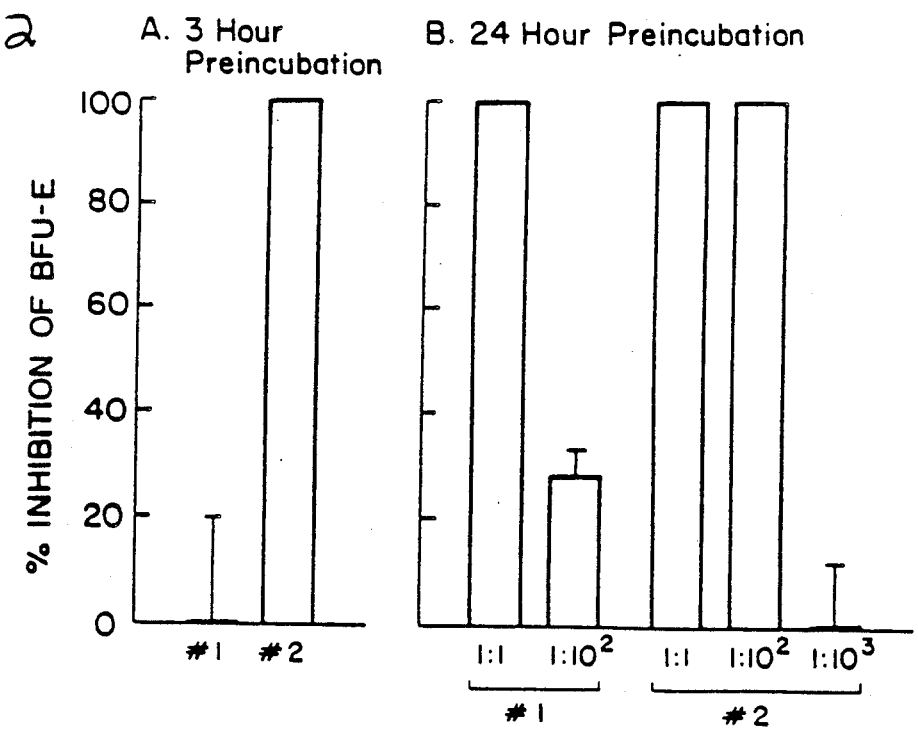
FIG. 2 is a schematic graph illustrating that the extent of inhibition on growth and differentiation of bone marrow cells is dependent both on concentration of the virus and on time of exposure in the assay of the present invention.

The findings graphically illustrated in FIG. 2 show that the extent of inhibition of growth and differentiation of bone marrow cells is dependent both on the concentration of the virus and on the time of exposure. The sera used in the three-hour incubation was diluted 1:1. Mononuclear cells were incubated with AB+control serum that lacked HBV or HBV DNA+sera for 3 or 24 hours; washed four times and plated into the BFU-E assay. Plotted are the mean values of three simultaneous determinations and the standard error of the mean. No inhibition of BFU-E was observed after three hours of preincubation of undiluted serum while complete suppression was seen after 20 hours of preincubation of undiluted serum but not serum diluted 1:100. Serum No. 2 that contains more virus than serum No. 1 completely inhibited BFU-E after three hours incubation when undiluted, but not at a 1:1000 dilution. Similar results were obtained with CFU-GM and CFU-E. To confirm that HBV is responsible for inhibition of the various hematopoietic stem cells, the HBV DNA positive sera was treated to inactivate or remove infectious HBV. Three conventional methods were used: heat, dialysis against urea and removal of HBV using a mouse monoclonal anti-HBs affinity column, as outlined below.

First, one ml of sera was incubated in a 100° C. water bath in an Eppendorf centrifuge tube for one minute and then allowed to cool to room temperature to inactivate the infectious HBV.

By a second technique, sera was placed in a dialysis membrane and dialized against 4 M urea or phosphate buffered saline (PBS) for 48 hours with two changes of dialysate, and then against three changes of PBS to inactivate the infectious HBV.

The HBsAg+HBV DNA+serum was repeatedly immunoabsorbed to a mouse monoclonal anti-HBs sepharose column. The serum eluate was concentrated to the original volume and sterilized by 0.22 um filtration. The column was washed with ten volumes of PBS and eluted with pH of 2.4 glycine-HCl buffer. The eluate was neutralized, dialyzed against PBS and concentrated to the original volume. The immunoabsorbed serum was demonstrated to have no HBV DNA by dot-blot analysis and less than 95% of initial HBsAg concentration and most likely lacks virus. In contrast, the eluate had both HBsAg and HBV DNA, and therefore, most likely contains virus.

Figure 3:
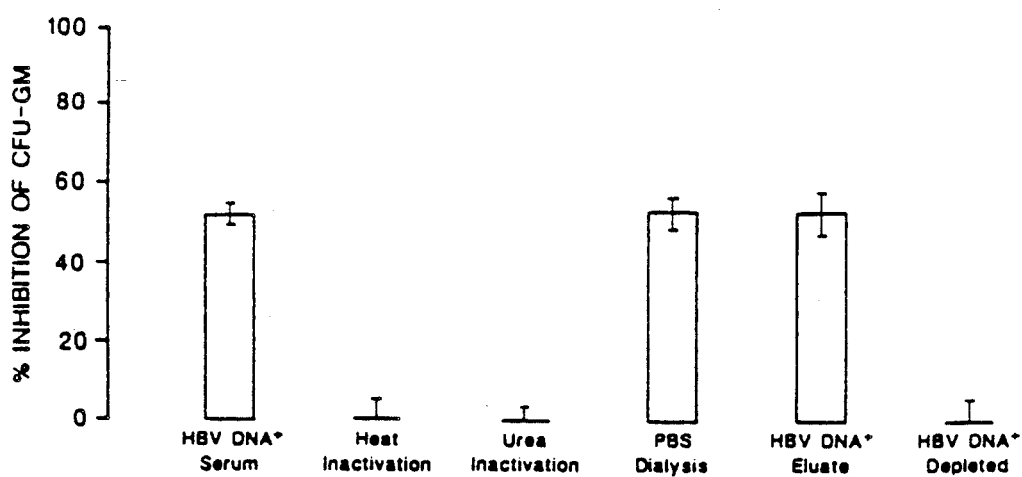
FIG. 3 illustrates the results of a series of tests performed to confirm the results of the assay of the present invention.

The effect of these treatments on HBV mediated suppression of CFU-GM are shown in FIG. 3. FIG. 3 shows the results of a series of tests that demonstrated that the inhibitory factor in the sample is HBV and not some other serum derived factor. Both heat inactivation and urea dialysis, which eliminate infectivity of HBV, removed the inhibitory effect of HBV DNA positive sera on CFU-GM. In contrast, dialysis of HBV DNA+sera against PBS did not suppress CFU-GM. Serum depleted of HBV DNA following passage through an anti-HBs immunoabsorption column no longer inhibited CFU-GM. The HBV DNA containing eluate recovered from the column markedly suppressed CFU-GM. Thus, the inhibitory activity of HBV containing sera coincided with HBV infectivity and the presence of HBsAg immunoreactivity and of HBV DNA.

FIG. 4 illustrates the inhibitory effect of hepatitis B virus on the growth and differentiation of bone marrow stem cells from leukemic cell line cells. Sample A contains no HBV and no antibody. Sample C contains HBV, but does not contain antibody to HBV. Sample C shows a 46% inhibition of colony growth as compared to Sample A.

FIG. 4 also shows that an antibody to the HBV reverses the inhibitory effect of the virus. Sample D, which contains HBV and antibody to HBV at full strength, shows very little suppression of colony formation (about 4%). As the antibody is diluted further, however, the inhibitory effect of the HBV becomes evident again (Samples E-G).

The invention may be embodied in other specific forms without departing from the spirit or essential characteristics therof. The present embodiments are therefore to be considered in all respects as illustrative and not restrictive, the scope of the invention being indicated by the appended claims rather than by the foregoing description, and there is no intention to exclude any equivalents thereof. Hence, it is recognized that various modifications are possible within the scope of the present invention as claimed.

What is claimed is:

1. A method for detecting the presence of hepatitis viruses in a sample of body fluid or biological preparation comprising:
   a) providing a source of live hepatitis virus-free cells obtained from bone marrow of peripheral blood;
   b) isolating mononuclear cells from the cells obtained in step a);
   c) enriching the mononuclear cells with a growth factor;
   d) incubating the mononuclear cells with the sample to be tested under conditions which promote the proliferation of mononuclear stem cells to form colonies;
   e) counting the number of colonies that arise from the incubation; and
   f) comparing the number colonies to a control to detect the presence of live hepatitis virus wherein the presence of live hepatitis virus is related to the inhibition of colony growth.

2. The method of claim 1 wherein the hepatitis virus-free bone marrow cells are obtained by aspiration from the iliac crest, from ribs or from peripheral blood of people with no serologic evidence of hepatitis virus infection.

3. The method of claim 1 wherein the mononuclear cells are preincubated or coincubated with the sample to be tested for a period of time sufficient for said mononuclear cells to take up any virus present in the sample prior to said incubation step, and wherein, prior to placing them in conditions which promote the proliferation of mononuclear stem cells to form colonies, the cells are washed to remove any virus which has not been taken up by the cells.

4. The method of claim 1 wherein the incubation step comprises placing the mononuclear cells in suspension culture and adding growth factors to the stem cell of interest to promote its proliferation to form colonies.

5. A method for detecting the presence of live Hepatitis B viruses in a sample of a body fluid or biological preparation comprising:
  a) providing a source of hepatitis B virus-free cells obtained from bone marrow or peripheral blood;
  b) isolating mononuclear cells from the cells obtained in step a);
  c) enriching the mononuclear cells with a growth factor;
  d) incubating the mononuclear cells with the sample to be tested under conditions which promote the proliferation of mononuclear stem cells to form colonies;
  e) counting the number of colonies that arise from the incubation; and
  f) comparing the number of colonies to a control to detect the presence of live hepatitis B virus wherein the presence of live hepatitis virus is related to the inhibition of colony growth.

6. The method of claim 5 wherein the hepatitis virus-free bone marrow cells are obtained by aspiration from the iliac crest or ribs or peripheral blood of a donor with no serologic evidence of hepatitis virus infection.

7. The method of claim 5 wherein the mononuclear cells are preincubated or coincubated with the sample to be tested for a period of time sufficient for said mononuclear cells to take up any virus present in the sample prior to said incubation step, and wherein, prior to placing them in conditions which promote the proliferation of mononuclear stem cells to form colonies, the cells are washed to remove any virus which has not been taken up by the cells.

8. The method of claim 5 wherein the incubation step comprises placing the mononuclear cells in suspension culture and adding growth factors to the stem cell of interest to promote its proliferation to form colonies.

9. A method for detecting the presence of live hepatitis viruses in a sample of a body fluid or biological preparation comprising:
  a) providing a source of hepatitis virus-free leukemic cell line cells;
  b) incubating the leukemic cell line cells with a sample to be tested under conditions which promote the proliferation of leukemic cell line cells to form colonies;
  c) counting the number of colonies that arise in culture; and
  d) comparing the number of colonies to a control to detect the presence of live hepatitis viruses wherein the presence of live hepatitis virus is related to the inhibition of colony growth.

10. The method of claim 9 wherein the leukemic cell line cells are preincubated or coincubated with the sample to be tested for a period of time sufficient for said leukemic cell line cells to take up any virus present in the sample prior to said incubation step, and wherein, prior to placing them in conditions which promote the proliferation of the leukemic cell line cells to form colonies, the cells are washed to remove any virus which has not been taken up by the cells.

11. A method for detecting the presence of live hepatitis B viruses in a sample of a body fluid or biological preparation comprising:
  a) providing a source of hepatitis virus-free leukemic cell line cells;
  b) incubating the leukemic cell line cells with a sample to be tested under conditions which promote the proliferation of leukemic cell line cells to form colonies;
  c) counting the number of colonies that arise in culture; and
  d) comparing the number of colonies to a control to detect the presence of live hepatitis B virus wherein the presence of live hepatitis virus is related to the inhibition of colony growth.

12. The method of claim 11 wherein the leukemic cell line cells are preincubated or coincubated with the sample to be tested for a period of time sufficient for said leukemic cell line cells to take up any virus present in the sample prior to said incubation step, and wherein, prior to placing them in conditions which promote the proliferation of the leukemic cell line cells to form colonies, the cells are washed to remove any virus which has not been taken up by the cells.

13. The method of claim 3 wherein the preincubation period is from one hour to overnight prior to the incubation step.

14. The method of claim 3 wherein the preincubation period is from 16-24 hours prior to the incubation step.

15. The method of claim 3 wherein the coincubation period occurs simultaneously with incubation step.

16. The method of claim 7 wherein the preincubation period is from one hour to overnight prior to the incubation step.

17. The method of claim 7 wherein the preincubation period is from 16-24 hours prior to the incubation step.

18. The method of claim 7 wherein the coincubation period occurs simultaneously with the incubation step.

19. The method of claim 10 wherein the preincubation period is from one hour to overnight prior to the incubation step.

20. The method of claim 10 wherein the preincubation period is from 16-24 hours prior to the incubation step.

21. The method of claim 10 wherein the coincubation period occurs simultaneously with the incubation step.

22. The method of claim 12 wherein the preincubation period is from one hour to overnight prior to the incubation step.

23. The method of claim 12 wherein the preincubation period is from 16-24 hours prior to the incubation step.

24. The method of claim 12 wherein the coincubation period occurs simultaneously with the incubation step.

* * * * *